(12) United States Patent
Koff et al.

(10) Patent No.: US 8,724,867 B2
(45) Date of Patent: May 13, 2014

(54) SYSTEM AND METHOD FOR MANAGEMENT AND DISTRIBUTION OF DIAGNOSTIC IMAGING

(75) Inventors: David Koff, Ontario (CA); Nadine Koff, Ontario (CA); Greg Butler, Nova Scotia (CA); Ian Maynard, Ontario (CA); Taras Vasylenko, Ontario (CA); Alex Pakka, Ontario (CA); Paul Pierre, Ontario (CA); Oleg Kovalchuk, Ontario (CA)

(73) Assignee: Realtime Radiology Inc., Ontario (CA)

( * ) Notice: Subject to any disclaimer, the term of this patent is extended or adjusted under 35 U.S.C. 154(b) by 154 days.

(21) Appl. No.: 13/260,748

(22) PCT Filed: Nov. 25, 2010

(86) PCT No.: PCT/CA2010/001898
§ 371 (c)(1),
(2), (4) Date: Jan. 10, 2012

(87) PCT Pub. No.: WO2011/063530
PCT Pub. Date: Jun. 3, 2011

(65) Prior Publication Data
US 2012/0243754 A1 Sep. 27, 2012

Related U.S. Application Data

(60) Provisional application No. 61/264,327, filed on Nov. 25, 2009.

(51) Int. Cl.
*G06K 9/00* (2006.01)
(52) U.S. Cl.
USPC .............................................. 382/128; 705/3
(58) Field of Classification Search
CPC ...... G06Q 50/22; G06Q 50/24; G06F 19/322; G06T 7/0012
USPC .............................. 382/100, 128–132; 705/3; 709/223–226, 303
See application file for complete search history.

(56) References Cited

U.S. PATENT DOCUMENTS

| 7,756,724 B2 * | 7/2010 | Gropper et al. ................... 705/2 |
| 2002/0019751 A1 * | 2/2002 | Rothschild et al. ............... 705/3 |

(Continued)

FOREIGN PATENT DOCUMENTS

EP 1016998 A2 7/2000

OTHER PUBLICATIONS

International Search Report from PCT/CA2010/001898, mailing date Mar. 8, 2011.

*Primary Examiner* — Shefali Goradia
(74) *Attorney, Agent, or Firm* — Thomas & Karceski, P.C.

(57) ABSTRACT

A method of distributing an image study to a chosen image reader is disclosed having steps of receiving an image study from an image producer at a third party communication module, sending a receive notification message to a messaging layer, sending a study available notification message from the messaging layer to a workload distribution engine wherein the available notification message includes extracted image study information pulled from study headers of the image study, identifying image study rules from the extracted image study information, applying an image study complexity to the image study based on the image study rules, calculating image reader complexities for a plurality of image readers subscribed to receive image studies from the image producer, each of the image reader complexities calculated using the image study complexity and an Image reader profile assigned to each of the plurality of accredited image readers, selecting the chosen image reader from the plurality of image readers based on the image reader complexities, assigning the image study to the chosen image reader, and displaying the image study on a user interface to the chosen image reader.

21 Claims, 6 Drawing Sheets

(56) References Cited

U.S. PATENT DOCUMENTS

| | | | |
|---|---|---|---|
| 2002/0143862 A1* | 10/2002 | Peterson | 709/203 |
| 2007/0067252 A1* | 3/2007 | Hengerer et al. | 707/1 |
| 2007/0118648 A1 | 5/2007 | Millefiorini | |
| 2009/0048869 A1 | 2/2009 | Tyler | |

* cited by examiner

SYSTEM AND METHOD FOR MANAGEMENT AND DISTRIBUTION OF DIAGNOSTIC IMAGING

RELATED US APPLICATION

This application claims the benefit of U.S. Provisional application No. 61/264,327 assigned to Real Time Radiology, assignee of the subject application, the contents of which are incorporated by reference.

FIELD OF THE INVENTION

The present invention relates generally to diagnostic imaging management and in particular to a system and method for coordinating diagnostic images and diagnostic interpretation services.

BACKGROUND OF THE INVENTION

Coordinating software products for diagnostic medical imaging and diagnostic interpreting services are known. Such coordinating software products are capable of collecting and distributing diagnostic medical images from medical image producers such as hospitals, clinics, laboratories and other medical imaging producers with access to medical imaging techniques or modalities to diagnostic medical imaging readers such as radiologists and other medical experts for interpretation and diagnosis. These products permit access to pre-arranged schedules of available resources with job orders to be done. Image producers use such software products to allot image studies to prospective medical imaging specialists to ensure their needs for medical image interpretation are met.

While the above-described scheduling software can be useful, improvements are of course desirable. For example, such tools do not allow medical imaging readers to subscribe to available work on a "first come-first served" basis while rewarding desirable behavior such as early commitment to coverage and preventing selection of only highly lucrative work. Nor do these scheduling systems allow a doctor to provide service without prior knowledge of what demand is required.

Existing scheduling and coordinating products do not reflect real world interactions between medical specialists and the medical facilities that they support. Presently available medical imaging coordinating products do not have a mechanism for allowing medical specialists who have previously reported a particular patient's images to view subsequent imaging studies from the same patient. Nor do such products allow for priority analysis by available doctors in real time.

It is therefore an object of the present invention to provide a system for supporting coordination of diagnostic imaging services with diagnostic imaging job orders that overcomes the above deficiencies.

SUMMARY OF THE INVENTION

According to one aspect there is provided a method of distributing an image study to a chosen image reader comprising receiving an image study from an image producer at a third party communication module, sending a receive notification message from a third party communication module to a messaging layer, sending a study available notification message from the messaging layer to a workload distribution engine wherein the available notification message includes extracted image study information pulled from study headers of the image study, identifying image study rules from the extracted image study information, applying an image study complexity to the image study based on the image study rules, calculating image reader complexities for a plurality of image readers subscribed to receive image studies from the image producer, each of the image reader complexities calculated using the image study complexity and an image reader profile assigned to each of the plurality of accredited image readers, selecting the chosen image reader from the plurality of image readers based on the image reader complexities, assigning the image study to the chosen image reader, and displaying the image study on a user interface to the chosen image reader.

According to another aspect there is provided a method of distributing an image study to an available image reader comprising receiving an image study from an image producer at a third party communication module, sending a receive notification message from a third party communication module to a messaging layer, sending a study available notification message from the messaging layer to a workload distribution engine wherein the available notification message includes extracted image study information pulled from study headers of the image study, identifying image study rules from the extracted image study information, and assigning the image study to the available image reader in the event that at least one image study rule indicates the image study has urgent priority.

According to another aspect there is provided a method of distributing an image study to a reserved image reader comprising receiving an image study from an image producer at a third party communication module, sending a receive notification message from a third party communication module to a messaging layer, sending a study available notification message from the messaging layer to a workload distribution engine wherein the available notification message includes extracted image study information pulled from study headers of the image study, identifying image study rules from the extracted image study information, and assigning the image study to the reserved image reader in the event that at least one image study rule indicates the image study is reserved for the reserved image reader.

According to another aspect there is provided a method for scheduling distribution of image studies produced by an image producer to an image reader comprising receiving a request from the image producer for coverage of image study workload during at least one coverage time period, receiving image reader available notifications from a plurality of image readers indicating the plurality of image readers have available time periods to provide coverage of image study workload, matching the at least one coverage time periods to the image readers having corresponding available time periods, and assigning image readers having corresponding available time periods receive the image studies during the at least one coverage time period.

According to yet another aspect there is provided an image distribution system comprising a third party communication module for receiving an image study from an image producer for interpretation by an image reader chosen from a plurality of image readers, each image reader having an associated image reader profile, the third party communication module creating a receive notification message, a messaging layer for communicating with the third party communication module, the messaging layer receiving the receive notification message and creating a study available notification message wherein the study available notification message includes extracted image study information pulled from study headers of the image study, a workload distribution engine communicatively connected to the messaging layer and receiving the study notification message, identifying image study rules from the extracted image study information, the workload distribution engine applying a study complexity to the image study based on the study rules, the workload distribution engine calculating image reader complexities for a plurality of image readers, each image reader complexity calculated using the study complexity and the associated image reader profile, the workload distribution engine choosing the image reader based on the calculated image reader complexity, the workload distribution engine routing the image study to the chosen image reader, and a user interface for receiving the image study routed from the study routing module and displaying the image study to the chosen image reader.

According to a further aspect there is provided a computer readable medium embodying a computer program for distributing an image study to a chosen image reader, the computer program code comprising program code for receiving an image study from an image producer at a third party communication module program code for sending a receive notification message from a third party communication module to a messaging layer, program code for sending a study available notification message from the messaging layer to a workload distribution engine wherein the available notification message includes extracted image study information pulled from study headers of the image study, program code for identifying image study rules from the extracted image study information, program code for applying an image study complexity to the image study based on the image study rules, program code for calculating image reader complexities for a plurality of image readers subscribed to receive image studies from the image producer, each of the image reader complexities calculated using the image study complexity and an image reader profile assigned to each of the plurality of accredited image readers, program code for selecting the chosen image reader from the plurality of image readers based on the image reader complexities, program code for assigning the image study to the chosen image reader, and program code for displaying the image study on a user interface to the chosen image reader.

According to a further aspect there is provided a computer readable medium embodying a computer program for distributing an image study to an available reader, the computer program code comprising program code for receiving an image study from an image producer at a third party communication module, program code for sending a receive notification message from a third party communication module to a messaging layer, program code for sending a study available notification message from the messaging layer to a workload distribution engine wherein the available notification message includes extracted image study information pulled from study headers of the image study, program code for identifying image study rules from the extracted image study information, and program code for assigning the image study to the available image reader in the event that at least one image study rule indicates the image study has urgent priority.

According to a further aspect there is provided a computer readable medium embodying a computer program for distributing an image study to a reserved image reader, the computer program code comprising program code for receiving an image study from an image producer at a third party communication module, program code for sending a receive notification message from a third party communication module to a messaging layer, program code for sending a study available notification message from the messaging layer to a workload distribution engine wherein the available notification message includes extracted image study information pulled from study headers of the image study, program code for identifying image study rules from the extracted image study information, and program code for assigning the image study to the reserved image reader in the event that at least one image study rule indicates the image study is reserved for the reserved image reader.

According to a still further aspect there is provided a computer readable medium embodying a computer program for distributing image studies produced by an image producer to an image reader, the computer program code comprising: program code for receiving a request from the image producer for coverage of image study workload during at least one coverage time period, program code receiving image reader available notifications from a plurality of image readers indicating the plurality of image readers have available time periods to provide coverage of image study workload, program code matching the at least one coverage time periods to the image readers having corresponding available time periods, and program code assigning image readers having corresponding available time periods receive the image studies during the at least one coverage time period.

BRIEF DESCRIPTION OF THE DRAWINGS

Embodiments will now be described more fully with reference to the accompanying drawings in which.

DETAILED DESCRIPTION OF THE EMBODIMENTS

Figure 1A:
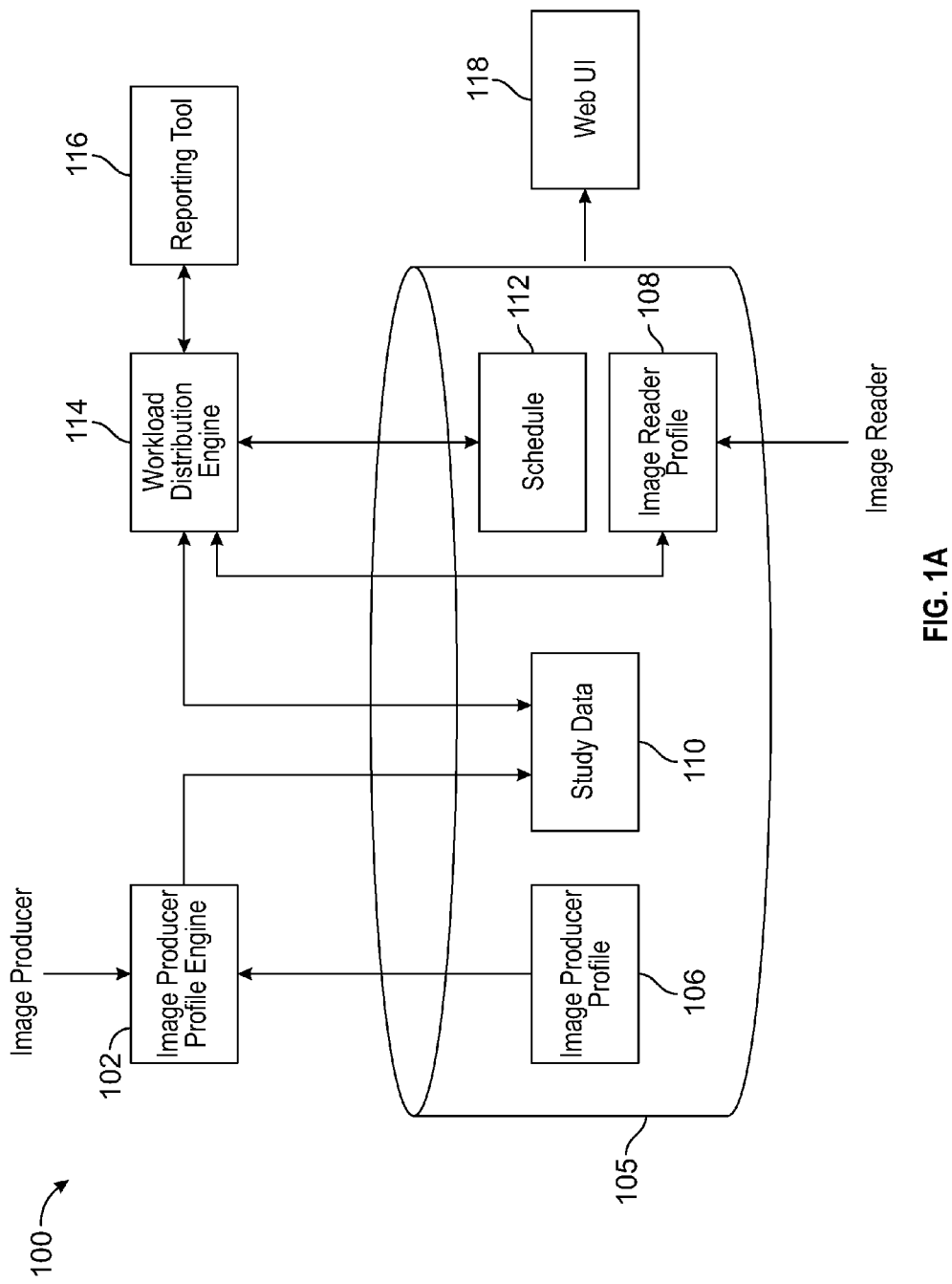
FIG. 1A is an exemplary block diagram of a system for coordinating and distributing service requests to service providers.

Turning to FIG. 1A, a system for coordinating and distributing medical imaging service requests from image producers to medical diagnostic imaging specialist or image reading service providers is shown and is generally identified by reference numeral 100. The system in this embodiment shows a producer profile engine 102 accessing a database 105. The database 105 stores an image producer profile 106, an image reader profile 108, study data 110, a schedule 112. A workflow distribution engine 114 also accesses the database 105 and a reporting tool 116. A web-based user interface 118 also accesses the database 105.

In the embodiment of the system 100 shown in FIG. 1A, image producers are able to access a producer profile 106 through the Web UI 118. Image producers may include but are not limited to hospitals, clinics, laboratories, and other medical facilities capable of producing medical diagnostic images for interpretation by an image reading service providers. Image reading service providers are usually radiologists but may include any medical specialist trained to interpret a medical image. The image reading service providers or image readers, in turn, access an image reader profile 108 through the web user interface (UI) 118.

The producer profile engine 102 allows the image producer to store study data 110 on the database 105 for a particular study. A study is a diagnostic medical image produced by an image producer to be read and interpreted by a medical specialist or image reading service provider. Study data 110 may include study history and study reports. Study history shows the image producer when a particular study was created, accessed, worked on, and by which medical specialist. Study reports are the written results of the study interpretation by an image reading service provider.

The web UI 118 allows image producers to provide information in the image producer profile 106 about their facilities, what modalities or imaging technologies they expect to be interpreted, a list of accredited image readers, and how they would like to be notified. An accredited image reader is an image reader whom the image producer has selected as an allowed image reader for that image producer's studies. An image producer profile 106 may also contain information such as but not limited to an identification number, location or physical address, volume of studies the image producer expects to send.

The web UI 118 allows image producers to specify the time periods for which they require image reader coverage and the volume of studies they expect to produce during this time period and store these requirements in the Schedule 112.

The image reader profile web UI 118 allows image readers to schedule their workloads. The image reader profile web UI 118 also allows image readers to provide information in their image reader profile 108 about their expected capacity of work, modalities and subspecialties in which they specialize, image producers for whom they do not agree to provide service, and how they would like to be notified. An image readers default expected capacity of work is specified in terms of number of units per hour for each specific study modality. For example, the value of zero for a specific study modality indicates that the image reader cannot provide interpretations for that modality.

The web UI 118 allows image reader to specify the time periods they are available to provide coverage, the volume of studies they are capable of interpreting and the particular image producers for which they are willing to provide coverage and store this information in the scheduling module 114

The workload distribution engine 114 accesses study data 110 from the database and matches the availability of image readers with image producers' schedules 112 using capacity and credentialing rules, and thereby matches imaging producer coverage requirements to image reading service provider availability.

The web UI 118 displays lists of studies received on the system. Such lists include studies received but not interpreted, studies assigned to specific image readers, studies interpreted and studies cancelled. The web UI also provides functions to launch the reporting tool 116 for a particular study, to cancel a study, reserve a study or manually assign a study to a specific image reader. In addition, the web UI 118 provides the ability to display the results of a study interpretation created in the reporting tool 116.

Figure 1B:
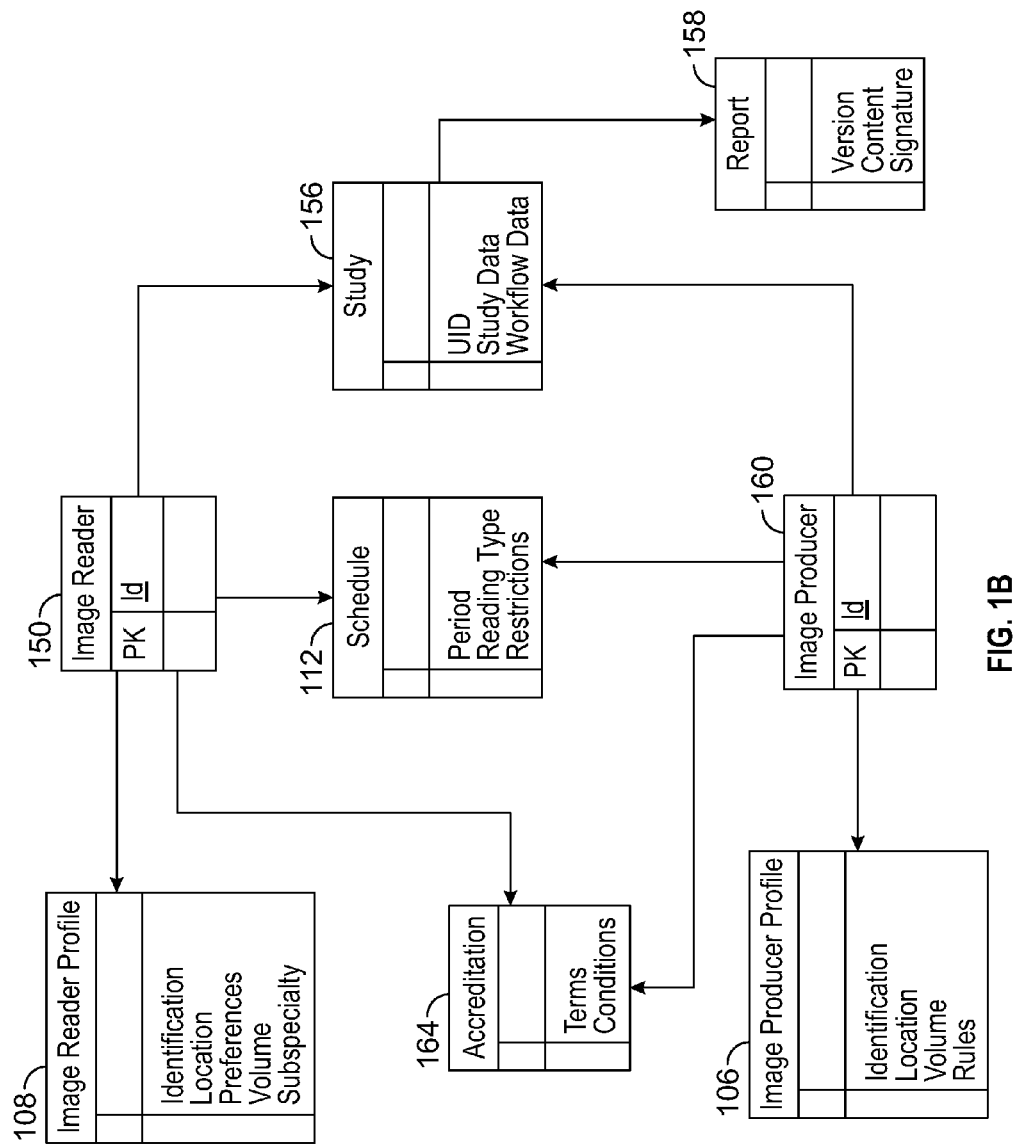
FIG. 1B is an entity relationship diagram of an embodiment of the components of FIG. 1A.

FIG. 1B is an entity relationship diagram illustrating the relationship between the components of the system in FIG. 1A. The image reader 150 has a unique image reader ID. Associated with the image reader 150 is an image reader profile 108 that includes such information as the image reader's full name, contact details, skills and volume information. Image reader 150 creates availability commitments in the schedule 112. Image readers 150 are assigned to interpret a study 156. A study 156 has attributes such as a unique study identifier, study data such as image producer ID, patient information, modality, study time and study description and workflow data such as indication to be interpreted (work item), status and priority. A report 158 is created for study 156 that is a work item. A report 158 can have information such as the signing image reader, version and specific interpretation content. Image producer 160 has a unique image producer ID. Associated with the image producer 160 is an image producer profile 106 that includes such information as contact details, expected volume, and rules to be applied by the producer profile engine 102 on receipt of a study from producer ID. Image producer 160 can create coverage requests in the schedule 112. Image producer 160 creates the study 156 to be transmitted to the system.

Credentialing is the process of indicating that image readers can provide coverage, view study information and create interpretation reports for particular image producers. Associations are defined by the system administrator in the system admin UI 244 and stored in the accreditation table 164 in the database 105.

Figure 2:
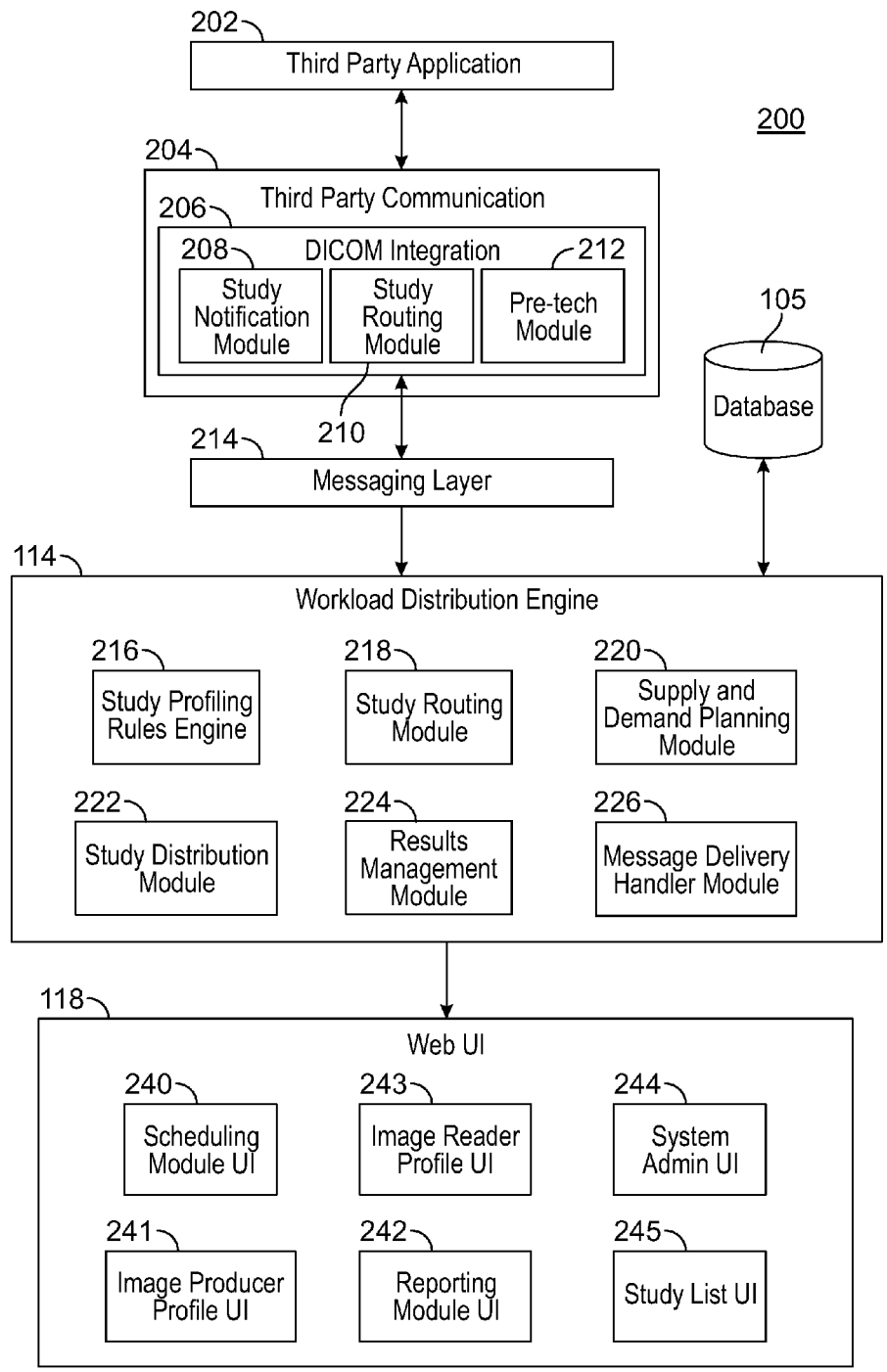
FIG. 2 is a block diagram of an embodiment of the system of FIG. 1A.

FIG. 2 shows an exemplary schematic diagram of an embodiment of the system for distributing medical image reading service requests from image producers to image reading service providers and is generally identified by the reference numeral 200. In FIG. 2, third party industry standard picture archive and communications system (PACS) applications 202 communicate with a third party communication module 204, which is able to accept and discern different kinds of image studies. The third party communication module 204 is also able to accept other third party studies using other kinds of communication protocols such as HL7. In this example, the third party communication module 204 receives and stores DICOM studies, creates notifications that a study has been received, issues DICOM study move commands, and issues DICOM study queries. In this example, the third party communications module 204 includes a DICOM integration module 206 that may include but is not limited to such modules as a study notification module 208, a study routing module 210 and a pre-fetch module 212. The study notification module 208 creates messages upon receipt of a study and transmits those messages onto the messaging layer 214. The study routing module 210 receives study routing instruction messages from the messaging layer 210 and instructs the third party communications module 204 to move the study to the instructed destination. The pre-fetch module 212 receives messages from the message Layer 214 on receipt of a study to query an industry standard third party application (PACS) 204 about the availability of other related studies and retrieve studies which are relevant to the receive study.

In another embodiment, the third party communication module 204 communicates with a messaging layer 214 directly, bypassing the DICOM Integration Module 206. The messaging layer 214 receives information about a study from the third party communication module 204, and delivers a notification message that a study is available to the workload distribution engine 114.

The notification message typically contains information pulled from the DICOM headers of the study, which originates within a DICOM integration module 206. This information in the notification message may include but is not limited to the patient ID, patient name, the image producer ID, the image producer's study identifier, study creation date, ordering department, and number of images in the study.

In turn, the messaging layer 214 interacts with the workload distribution engine 114. In this example, the workload distribution engine 114 has a study profiling rules engine 216, a study routing module 218, a supply and demand planning module 220, a study distribution module 222, a results management module 224, and messaging delivery handler module 226. The study profiling rules engine 216 performs actions on the received study notifications from the messaging layer 214. Once these actions are performed, the study profiling rules engine 216 is able to determine if a particular study may be routed, what the priority of the study should be and if the study should be considered as an study to be interpreted (or a workitem) or a study for reference.

The study routing module 218 uses information received as part of the study, such as producer ID and in certain embodiments the assigned image reader as determined by the Study Distribution Module 222 to create instruction messages to be passed via the Message Layer 214 to cause the third party communications module 204 to move the study to a specific third party application (PACS) 202 to be displayed.

The supply and demand planning module 220 consumes imaging producer coverage request information from the Schedule 112, image reader coverage availability information from the schedule 112, image reader credential information from the producer and reader profiles and matches producer requests to image reader availability and stores the agreement for service for each producer and reader intersection. The supply and demand planning module 220 create alerts through the scheduling module UI 240 if the declared available image reader capacity is insufficient to provide interpretations for the declared producer requests.

At specified intervals, the supply and demand planning module 220 provides notifications to image readers of upcoming coverage commitments. In one embodiment, these notifications at specified intervals may be fulfilled through Internet calendar messages transmitted using the message delivery handler module 226 via e-mail, using the image reader's e-mail address stored in the image reader's profile 108. In an alternative embodiment, upcoming coverage commitment notifications are sent through periodic e-mail messages via the message delivery handler module 226 showing rolling upcoming coverage commitments in accordance with the periodic notification values stored in an image reader's profile 108 stored on the database 105.

When an order from an image producer is created, the order is passed to the study distribution module 222. The study distribution module 222 provides study distribution from multiple study image producers to multiple study consumers (readers). This distribution is based on a set of rules and weighting decisions such as the amount of outstanding work for each image reader, the priority of the study and service operator defined adjustment values.

The workload distribution engine 114 corresponds with a web user interface 118 which image producers, image readers and system administrators can access. The web user interface 118 may include a scheduling module user interface (UI) 240, the image producer profile user interface (UI) 241, the image reader profile user interface (UI) 243 and a reporting module user interface (UI) 242.

The scheduling module UI 240 provides a calendar oriented view for image producers to declare their coverage needs for specific time periods or for multiple recurring time periods. Image producers can change the expected study volume information stored in their image producer profile 106 for each specific coverage request. A similar calendar oriented view is available for image readers to declare their coverage availability for specific periods or Multiple recurrent periods. If the supply and demand planning module 220 determines that the sum of the available supply of image reader capacity is greater than or equal to the sum of the declared image producer demand, the user interface changes colour for the time period to indicate adequate coverage.

The image producer profile UI 241 and the image reader profile UI 243 provide screens for producers and reader to maintain their producer profile and image reader profile information such as default volumes, contact information and in the case of the reader profile, subspecialty areas and excluded producer sites. The information entered into the user interface is stored in the producer profile 106 and image reader profile 108 respectively.

The study list UI 245 provides lists and functions to display the studies available on the system for reporting, the status of studies, the assignment history of a study, to which reader the study has been assigned and depending on the permissions of the user, the ability display the results of an interpretation or cancel a previously study designated for interpretation. Studies in the study list module are retrieved from study data 110

The system admin UI 244 provides input methods to create links between image producers and image reader e.g. accreditations 164, define producer profile engine 102 rules and parameters, define study distribution module 222 rules and parameters and create image producers IDs and image reader IDs.

The reporting module UI 242 is launched from the study list UI 245 to provide an input method to document the results of a study interpretation and to launch the appropriate diagnostic imaging viewer to display the image data associated with the study. Input forms can be different depending on data received in the study available message such as study description, modality and producer ID.

In one embodiment, information is acquired, transferred or modified prior to the creation of an order for study by an image reader. The study profiling rules engine 216 references study profiling information stored on the database 105 for each image producer ID to determine rules and actions applicable for study available notifications received from that image producer. Rules and actions may be used singularly or in combination. In another embodiment, the study profiling rules engine 216 will retrieve the image producer ID information from the received study notification message sent from the messaging layer 214 and generate a study forward message to the DICOM integration module 206, which will cause the third party communications module 204 to forward the received study to a target interpretation PACS system defined in the producer profile.

The study distribution module 222 matches image readers' availability with image producer schedules, credentialing, and workload rules to assign studies to image readers. When a study arrival notification has been received and a study enters the workload distribution engine 114, the study distribution module 222 assigns complexities to the study, sums the complexities and compares the amount of work assigned to each image reader. The complexities are derived from a combination of study fee revenue and estimated time to complete the study. An individual study's complexities may also be based on information derived from the received study, study description, study modality, and the body part that has been imaged in the study.

In another embodiment, the DICOM integration module 206 initiates a query to identify the availability of related studies stored in third party application (PACS) 202. If there is a related study, the pre-fetch module 212 will retrieve patient ID, study description, study modality, and sending PACS system information from the received study notification message as well as target PACS system information stored in the image producer profile 106. The study routing module 216 sends a command message to the pre-fetch module 212 of the DICOM Integration Module 206 to cause the third party communication 204 to issue a constrained DICOM Query message to the target PACS system. The received information is used by the pre-fetch module 212 to cause the third party communication 204 to issue a DICOM move command to the producer PACS. The producer PACS then sends the identified studies to a system defined related studies DICOM Application Entity Title. Upon receipt of each series of each related study, the DICOM integration module 206 will generate a "Study Available Event" and transmit this information using the messaging layer 214 to the study profiling rules engine 216 including the related studies logical address information (e.g. DICOM Application Entity Title). The study profiling rules engine 216 will use the related studies logical address information to determine that the retrieved study is for reference only and not create an order for interpretation. The study profiling rules engine 216 will issue a "Study Forward" message through the messaging layer 214 to the study routing module 210 which will cause the third party communication 204 to forward the study to a target interpretation PACS system defined in the image producer profile stored data 106.

In a further embodiment, instead of the DICOM integration module 206 soliciting related studies from the image producer, the image producer may send studies for interpretation and related information together unsolicited. In this instance, the study profiling rules engine 216 references the time the study was created from the notification message to determine which of the studies sent is to be interpreted and which are the related information. The related information is typically studies which have been previously interpreted prior to the study to be read and interpreted. The study profiling rules engine 216 will set the study status stored in the study information 156 to the value of "cancelled" for the related information. This can be manually converted to a valid study through a system admin UI 244 by a system administrator if the study profiling rule incorrectly profiled the study. In turn, the system administrator can also manually cancel studies deemed to be valid studies if advised to do so by the image producer.

In a still further embodiment, the study profiling rules engine 216 may use the image producer ID in the image producer profile 106, the time the study was received by the system, study priority, and the department of the image producer which has ordered the study to apply study priority rules to elevate or lower the priority of the study. This is discussed in detail in FIG. 4.

Figure 3:
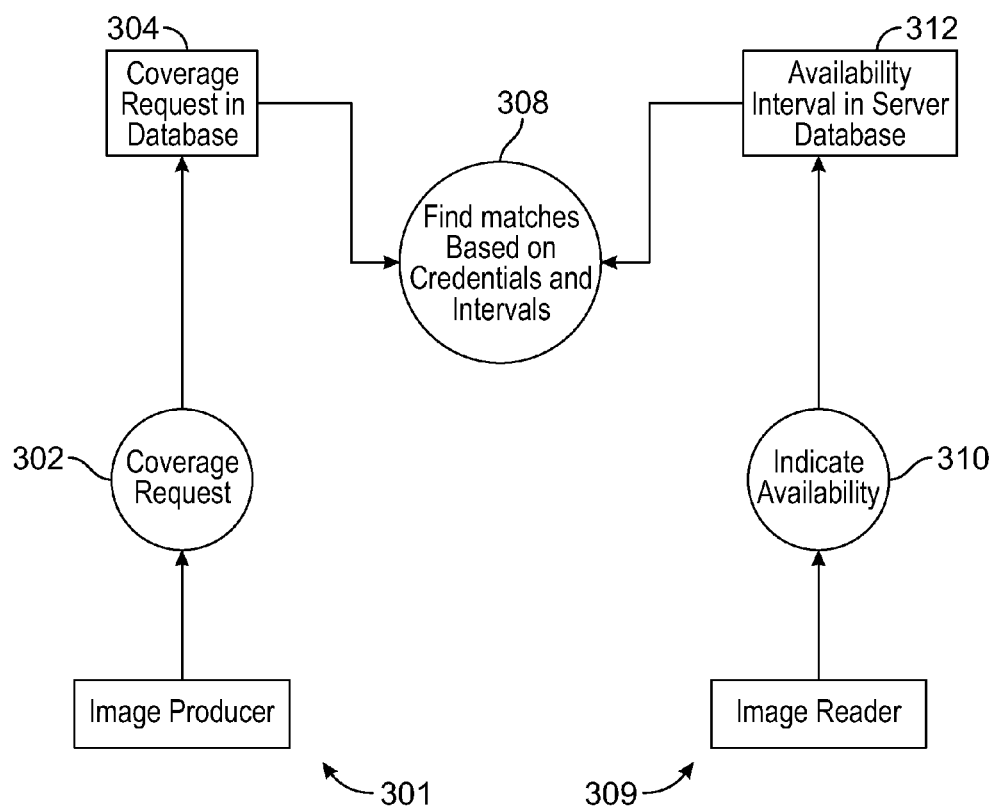
FIG. 3 is a schematic diagram of an embodiment of the components of the supply and demand planning module of FIGS. 1A and 1B.

FIG. 3 is a schematic diagram showing the relationship between image producer and image reader for purposes of supply and demand planning and documentation of coverage commitments. In FIG. 3, an image producer 301 makes a coverage request 302 which is sent to the coverage request 304 section of the schedule database 112. On the other side, an image reader 309 indicates availability 310 through the scheduling module UI 240. The availability notification 312 is sent to the interval section 312 of the scheduling database 112. Matches are made 308 by the supply and demand planning module 220 for the image producer's coverage request, and matches for the image reader's availability notification using the credentialing criteria, scheduling commitments found in the image reader's profile 108 and the image producer's profile 106.

Figure 4:
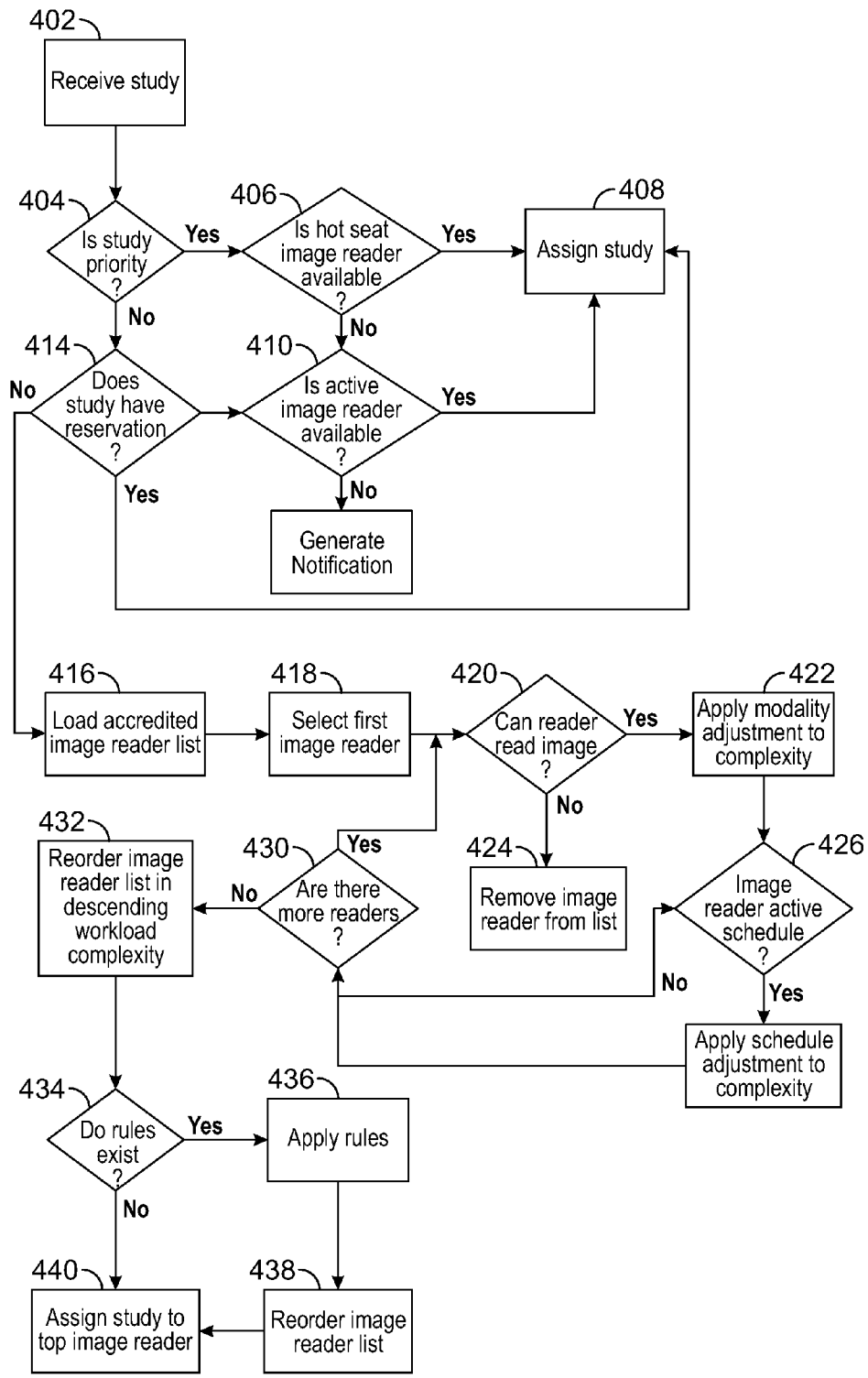
FIG. 4 is an exemplary flow diagram showing the method used by the components of FIG. 2.

FIG. 4 is a detailed flow chart of how the study distribution module 222 of the workload distribution engine 114 distributes studies. In step 402, a study is received by the workload distribution engine 114. In step 404, the workload distribution engine 114 checks the study priority as stored in the study information 156 after applying rules in the producer profile engine 102. A priority study is a study which must be completed immediately. It will take precedence over other studies due to the urgency the results from the study are needed. In the producer profile engine 102, study priority may be determined by the time at which the study arrives. For example, an image producer may request that if a study is sent by the image producers facilities after midnight, the study is deemed a priority. Priority may also be determined by which department or which doctor requires the study. For example, if the received study comes from an image producer's emergency department, it may be deemed a priority. An alternative way of determining priority may be based on the modality and body part with which the study is concerned. For example, an image producer may require that all magnetic resonance imaging (MRI) scans of the brain be deemed as priority studies.

In step 406, if the study is a high priority, the workload distribution engine 114 determines if the "hot seat" image readers are available to analyze and interpret the study. A hot seat image reader is an image reader who was the earliest to subscribe to coverage in the supply and demand planning module 220 for a specific image producer and who is logged into the service at the time that a priority study is received. For example, a first image reader has subscribed to work on studies from a first image producer on a particular day and time period and a second image reader has subscribed to the first and a second image producer on the same day and time period. If both the first and second image readers are logged in, then the first image reader will be the hot seat image reader for the first image producer while the second image reader is the hot seat image reader for the second image producer. The first reader will receive a study complexity adjustment to be applied to his complexity threshold for being hot seat reader. The first reader will receive an additional adjustment by the study distribution module for logging in at the specified time. If the first image reader is not logged on, then the second image reader is the hot seat image reader for both image producers and the first reader will not be assigned adjustments to his complexity threshold.

In step 408, if a hot seat image reader is available and the study is high priority, the workload distribution engine 114 assigns the study without regard for readers' outstanding complexity and complexity thresholds. In step 410, if a hot seat image reader is not available, the workload distribution engine 114 determines if there are any active accredited image readers logged on to the system. If there is an active image reader logged on to the system, then the study distribution module 222 will assign the study to that active image reader in step 408. If no active image reader is available to read the priority study, then the study is held in a "free" state until an active image reader is available.

If in step 404, the study is not a priority study, then in step 414, the study distribution module 222 will determine if the study is reserved for a particular image reader. If the study is reserved for a particular image reader, then the workload distribution engine 114 will assign the study to that particular image reader in step 408.

A study is reserved for a particular image reader in one of several ways. In one method a study may become reserved for a particular image reader if a particular image reader has previously viewed medical images from a certain patient, a reservation may be made in automatically by the study distribution module 222 that any future image studies of that patient, within a defined time period should be sent to that image reader regardless of whether the image reader's thresholds have been met. When a new study arrives that is of a previous patient, as indicated in the study available message the study distribution module 222 matches the patient ID to previous studies and routes the new study to the image reader listed in the previous study. In another example, an image producer may consult with an image reader prior to performing the imaging examination. In this case, the image producer identifies the hot seat reader and his contact information through the Study List UI 245 of the Web UI 118. The image producer contacts the hot seat reader and communicates the patient ID of the patient that will be imaged to the hot seat radiologist. The hot seat reader may enter the patient ID into the image reader profile UI 243 via the Web UI 118. The study distribution module creates a reservation token for the patient and matches the patient token to the patient information received in the study notification message when the study eventually arrives.

If the study is not reserved for a particular image reader, then in step 416, the workload distribution engine 114 loads a list of accredited image readers for the image producer that created the study. In step 418, the workload distribution engine 114 selects the first image reader in the list and then in step 420 determines if the image reader is able to read the study. An image reader is able to read the study if the image reader's profile 108 indicates that the image reader has experience in the modality of that study. An image reader's ability to read a study may also be affected by the image reader's subspecialties. For example if an image reader has a subspeciality in pediatric imaging, this would affect the image reader's ability to read a study of a geriatric patient. If the image reader is able to read the study, then in step 422, the study distribution module 222 applies a modality complexity adjustment to the study to define the studies complexity. Complexity adjustment is identified by apply the complexity weight associated with the any combination of the modality, body part examined and study description information included in the study available message. If in step 420, the image reader is not able to read the study, then that image reader will be removed from the list of image readers in step 424.

In step 426, the study distribution module 222 determines if the image reader has an active schedule. An image reader has an active schedule if the image reader has subscribed to the image producer's coverage request for the allotted time slot that the study has been received. If the image reader has an active schedule, then in step 428, the study distribution module 222 applies a schedule adjustment to the image reader's workload outstanding workload complexity. If the image reader has been logged in longer than other readers and additional adjustment is applied to the reader's outstanding workload complexity. If image reader was the first to subscribe to the image producer's coverage request then a third adjustment may be applied. In step 430, the study distribution module 222 moves to the next image wader in the list and performs steps 420 to 428 on the next image reader.

Steps 420 to 428 repeat until in step 430 the workload distribution engine 114 comes to the end of the accredited image reader list. In step 432, the workload distribution engine 114 reorders the accredited image reader list in descending order of outstanding workload complexity. In step 434, the study distribution module 222 determines if the study has any pre-existing rules. These rules may include but are not limited to the settings in an image producer profile 106, the settings in the image reader profile 108, the time interval, and study data. An image producer profile 106 may have a rule set for example, that all studies of a particular modality between certain hours are to be assigned to specific image readers regardless of their online status. An image reader profile 108 may have a rule set that declares the image reader's subspecialty or what body part images an image reader will accept. A time interval rule may include but is not limited to such rules as studies between certain hours are to be read by a certain group of image readers. A study data rule may include but is not limited to such rules as studies of a particular modality may only be assigned to certain readers.

If rules exist, then in step 436, the study distribution module 222 applies the rules. In step 438, the study distribution module 222 removes candidate readers who do not fit within the rules, and then reorders the list with the remaining candidates in reverse or according to outstanding complexity. In step 440, the workload distribution engine 114 assigns the study to the image reader at the top of the list or the image reader with the least adjusted outstanding complexity that is within the outstanding complexity threshold. If rules do not exist in step 436, then the workload distribution engine 114 assigns the study to the image reader at the top of the list or the image reader with the least adjusted outstanding complexity that is within the outstanding complexity threshold in step 440. If no reader has an adjusted outstanding complexity below the outstanding complexity threshold set within the study distribution module, then the study is not assigned and the distribution service 222 begins again at step 416

Figure 5:
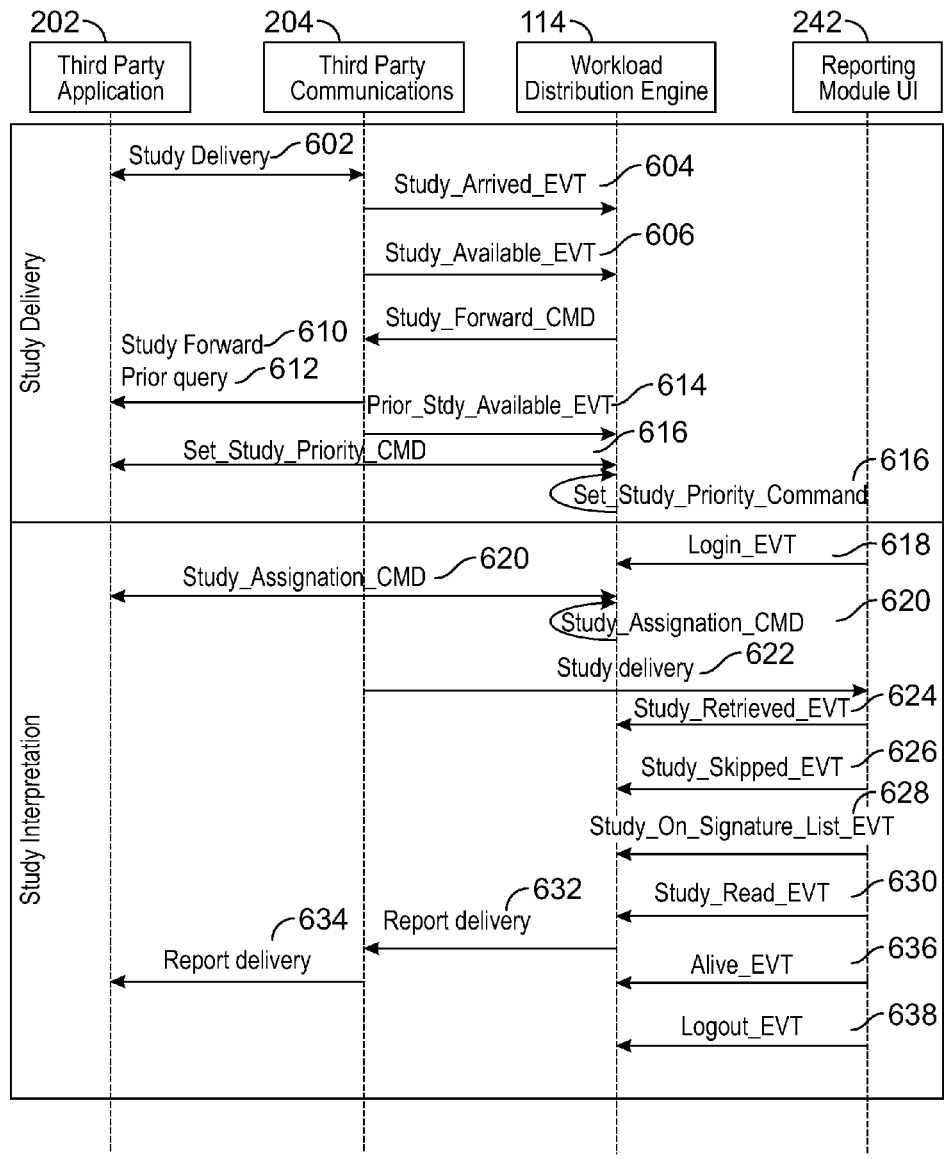
FIG. 5 is a sequence diagram showing an exemplary workflow between image producers and image readers using the system in FIG. 2.

FIG. 5 is a sequence diagram depicting the message flow between image producers 301 third party application 202 and image readers Reporting Module UI 242 using the system in FIG. 2. Image producer 301 third party application 202 sends a study to the third party communications module 204 as indicated by arrow 602. The third party communications module 204 sends a study arrived notification to the workload distribution engine 114 as indicated by arrow 604. The third party communications module 204 sends a study available notification to the workload distribution engine as indicated by arrow 606. The study available notification contains information for interpretation to the workload distribution engine 114 for determining to which image reader the study should be assigned. This information may include but is not limited to patient name, patient ID, study date, study description, body part examined, image producer name, image producer ID, referring physician. In arrow 610, a study forward notification is sent from the third party communications module 204 to the third party application 202. The study forward notification instructs the image producer interface to forward the study to a specific destination DICOM Application Entity Title. In arrow 612, the third party communications module 204 sends a query for prior relevant studies to the third party application 202 and instructs the third party application 202 to send the resultant studies to a specific DICOM Application entity Title. The third party communications module 204 sends a prior study available event to the workload distribution engine 114 as indicated by arrow 614. This event passes information about regarding whether the study is a work item or for reference. Work items are studies which require an interpretation report to be created by an image reader. Reference items are other imaging studies for the same patient, similar body parts and same or related modalities. Reference items are used by the image reader to determine if an item identified on the imaging study to be interpreted existed prior to the current study and if the identified item has changed in the interval between the acquisition of the reference study and the study to be interested. Reference items are commonly referred to as prior studies or priors. The workload distribution engine 114 sends a set study priority command to the Study List UI 245 as indicated in arrow 616 or to the third party application 202 as indicated by arrow 616 as required. In this command, instructions are sent by the study profile engine 216 within the workload distribution engine 114 to set the study priority. This occurs when the study status is not initially sent with the study. The reporting module UI 242 sends an image reader login event to the workload distribution engine 114 as indicated in arrow 618. A login event passes the login information of the image reader who has logged into the system, allowing the workload distribution engine 114 to know that that image reader is available to receive assignments. A study assignation command as demonstrated in arrow 620 is sent from the workload distribution engine 114 to the third party application 202 if reporting is done external to the system or to the Study List UI 242 if reporting is done internal to the system. This command indicates that the study should be available on a specific image reader's study list 242 or equivalent element of third party application 202. A study retrieved event is sent from the reporting module UI 242 to the workload distribution engine 114 as indicated in arrow 624. This event indicates that the study has been retrieved by the image reader for reading and interpretation. Arrow 626 indicates a study skipped event. This event signifies that the study has been closed but not interpreted. The workload distribution engine 114 will consider the study available for reassignment. An on hold event is sent from the reporting module UI 242 to the workload distribution engine as indicated in arrow 628. This event informs the workload distribution engine 114 that the study does not have a final interpretation by the image reader, but the study is also not available for reassignment. A study read event is sent from the reporting module UI 242 to the workload distribution engine 114 as indicated in arrow 630. This informs the workload distribution engine 114 that the interpretation of the study has been completed. Arrow 632 indicates a report delivery from the workload distribution engine 114 to the Third Party Communication 204. The report is further delivered to the image producer 301 third party application 202 as indicated by arrow 634. An availability notification is sent from the reporting module UI242 to the workload distribution engine 114 as indicated by arrow 636. This notification informs the workload distribution engine 114 that the image reader continues to be available to interpret more studies. Arrow 638 indicates a logout event passed from the reporting module UI 242 to the workload distribution engine 114. When the workload distribution engine 114 receives a notification that an image reader has logged out of the system, the workload distribution engine 114 will unassign studies and stop assigning new studies to that image reader, making those studies available to other logged in image readers.

Although the embodiments described herein could apply to distribution and management of medical imaging and medical imaging interpretation, one of skill in the art will appreciate that these techniques could be applied to other medical diagnostic management systems, for example, electrophysiology, dermatology, cardiology or pathology.

Although embodiments have been described, those of skill in the art will appreciate that variations and modifications may be made without departing from the spirit and scope thereof as defined by the appended claims.

What is claimed is:

1. A method of distributing an image study to a chosen image reader comprising:
   receiving an image study from an image producer at a third party communication module;
   sending a receive notification message from a third party communication module to a messaging layer;
   sending a study available notification message from the messaging layer to a workload distribution engine wherein the available notification message includes extracted image study information pulled from study headers of the image study;
   identifying image study rules from the extracted image study information;
   applying an image study complexity to the image study based on the image study rules;
   calculating image reader complexities for a plurality of image readers subscribed to receive image studies from the image producer, each of the image reader complexities calculated using the image study complexity and an image reader profile assigned to each of the plurality of accredited image readers;
   selecting the chosen image reader from the plurality of image readers based on the image reader complexities;
   assigning the image study to the chosen image reader; and
   displaying the image study on a user interface to the chosen image reader.

2. The method of claim 1 wherein the selecting step further comprises:
   sorting the plurality of image readers in according to the image reader complexities from a lowest complexity to a highest complexity; and
   selecting from the sorted plurality of image readers an image reader with the lowest complexity to be the chosen image reader.

3. The method of claim 1 wherein the calculating step further comprises extracting parameters from the image reader profile and assigning a complexity value to the parameters, the parameters selected from a group of a reader modality, a reader outstanding workload, a reader session length, a reader schedule information, and a reader subscription information.

4. A method of distributing an image study to an available image reader comprising:
   receiving an image study from an image producer at a third party communication module;
   sending a receive notification message from a third party communication module to a messaging layer;
   sending a study available notification message from the messaging layer to a workload distribution engine wherein the available notification message includes extracted image study information pulled from study headers of the image study;
   identifying image study rules from the extracted image study information; and
   assigning the image study to the available image reader in the event that at least one image study rule indicates the image study has urgent priority.

5. The method of claim 4 wherein the assigning step further comprises identifying the available Image reader from a plurality of image readers available to receive and interpret the image study when the image study is routed.

6. A method of distributing an image study to a reserved image reader comprising:
   receiving an image study from an image producer at a third party communication module;
   sending a receive notification message from a third party communication module to a messaging layer;
   sending a study available notification message from the messaging layer to a workload distribution engine wherein the available notification message includes extracted image study information pulled from study headers of the image study;
   identifying image study rules from the extracted image study information; and
   assigning the image study to the reserved image reader in the event that at least one image study rule indicates the image study is reserved for the reserved image reader.

7. A method for scheduling distribution of image studies produced by an image producer to an image reader comprising:
- receiving a request from the image producer for coverage of image study workload during at least one coverage time period;
- receiving image reader available notifications from a plurality of image readers indicating the plurality of image readers have available time periods to provide coverage of image study workload;
- matching the at least one coverage time period to the image readers having corresponding available time periods; and
- assigning image readers having corresponding available time periods receive the image studies during the at least one coverage time period.

8. The method of claim 7 further comprising calculating weights based on summing all coverage time periods and all available time periods to determine whether all requests or coverage time periods are met.

9. The method of claim 8 wherein in the event that all coverage time periods are not met a system administrator is notified.

10. An image distribution system comprising:
- a third party communication module for receiving an image study from an image producer for interpretation by an image reader chosen from a plurality of image readers, each image reader having an associated image reader profile, the third party communication module creating a receive notification message;
- a messaging layer for communicating with the third party communication module, the messaging layer receiving the receive notification message and creating a study available notification message wherein the study available notification message includes extracted image study information purled from study headers of the image study;
- a workload distribution engine communicatively connected to the messaging layer and receiving the study notification message, identifying image study rules from the extracted image study information, the workload distribution engine applying a study complexity to the image study based on the study rules, the workload distribution engine calculating Image reader complexities for a plurality of image readers, each image reader complexity calculated using the study complexity and the associated image reader profile the workload distribution engine choosing the image reader based on the calculated image reader complexity, the workload distribution engine routing the image study to the chosen image reader; and
- a user interface for receiving the image study routed from the study routing module and displaying the image study to the chosen image reader.

11. The system of claim 10 further wherein the user interface has a reporting module for inputting interpretation results of the image study made by the chosen image reader.

12. The system of claim 10 wherein the workload distribution engine assigns the image study to an available image study reader in the event that at least one image study rule indicates the image study has urgent priority.

13. The system of claim 10 wherein the workload distribution engine identifies the available image reader from a plurality of image readers available to receive and interpret the image study when the image study is routed.

14. The system of claim 10 wherein the workload distribution engine assigns the image study to a reserved image reader in the event that at least one image study rule indicates the image study is reserved for the reserved image reader.

15. The system of claim 10 wherein the workload distribution engine further comprises a study distribution module for sorting the plurality of image readers in according to the image reader complexities from a lowest complexity to a highest complexity and selecting from the sorted plurality of image readers an image reader with the lowest complexity to be the chosen image reader.

16. The system of claim 10 wherein the workload distribution engine extracts parameters from the image reader profile and assigns a complexity value to the parameters, the parameters selected from a group of a reader modality, a reader outstanding workload, a reader session length, a reader schedule information, and a reader subscription information.

17. The system of any one of claims 10 to 16 further comprising a supply and demand module for matching requests for study workload coverage from the image producer during a coverage time period to image reader available notifications from a plurality of image readers indicating the plurality of image readers have available time periods to provide coverage of image study workload, the scheduling module assigning image readers having corresponding available time periods receive the image studies during the at least one coverage time period.

18. A non-transitory computer readable medium embodying a computer program for distributing an image study to a chosen image reader, the computer program code comprising:
- program code for receiving an image study from an image producer at a third party communication module;
- program code sending a receive notification message from a third party communication module to a messaging layer;
- program code for sending a study available notification message from the messaging layer to a workload distribution engine wherein the available notification message includes extracted image study information pulled from study headers of the image study;
- program code for identifying image study rules from the extracted image study information;
- program code for applying an image study complexity the image study based on the image study rules:
- program code for calculating image reader complexities for a plurality of image readers subscribed to receive image studies from the image producer, each of the image reader complexities calculated using the image study complexity and an image reader profile assigned to each of the plurality of accredited image readers;
- program code for selecting the chosen image reader from the plurality of image readers based on the image reader complexities;
- program code for assigning the image study to the chosen image reader; and
- program code for displaying the image study on a user interface to the chosen image reader.

19. A non-transitory computer readable medium embodying a computer program for distributing an image study to an available reader, the computer program code comprising:
- program code for receiving an image study from an image producer at a third party communication module;
- program code for sending a receive notification message from a third party communication module to a messaging layer;
- program code for sending a study available notification message from the messaging layer to a workload distribution engine wherein the available notification message includes extracted image study information pulled from study headers of the imago study;

program code for identifying image study rules from the extracted image study information; and program code for assigning the image study to the available image reader in the event that at least one image study rule indicates the image study has urgent priority.

20. A non-transitory computer readable medium embodying a computer program for distributing an image study to a reserved image reader the computer program code comprising: program code for receiving an image study from an image producer at a third party communication module;

program code for sending a receive notification message from a third party communication module to a messaging layer;

program code for sending a study available notification message from the messaging layer to a workload distribution engine wherein the available notification message includes extracted image study information pulled from study headers of the image study;

program code for identifying image study rules from the extracted image study information; and program code for assigning the image study to the reserved image reader in the event that at least one image study rule indicates the image study is reserved for the reserved image reader.

21. A non-transitory computer readable medium embodying a computer program for distributing image studies produced by an image producer to an image reader, the computer program code comprising:

program code for receiving a request from the image producer for coverage of image study workload during at least one coverage time period;

program code receiving image reader available notifications from a plurality of image readers indicating the plurality of image readers have available time periods to provide coverage of image study workload;

program code matching the at least one coverage time periods to the image readers having corresponding available time periods; and program code assigning image readers having corresponding available time periods receive the image studies during the at least one coverage time period.

* * * * *